(12) United States Patent
Lui et al.

(10) Patent No.: US 8,342,193 B2
(45) Date of Patent: Jan. 1, 2013

(54) FLEXIBLE DENTAL FLOSS APPLICATOR AND INTERDENTAL GUM STIMULATOR

(76) Inventors: Wai-Kuen Lui, Shatin (HK); William Wai-Shing Lui, Cortlandt Manor, NY (US)

( * ) Notice: Subject to any disclaimer, the term of this patent is extended or adjusted under 35 U.S.C. 154(b) by 1182 days.

(21) Appl. No.: 10/593,701

(22) PCT Filed: Mar. 18, 2005

(86) PCT No.: PCT/US2005/008967
§ 371 (c)(1),
(2), (4) Date: Sep. 19, 2006

(87) PCT Pub. No.: WO2005/092237
PCT Pub. Date: Oct. 6, 2005

(65) Prior Publication Data
US 2007/0157946 A1      Jul. 12, 2007

Related U.S. Application Data

(60) Provisional application No. 60/554,636, filed on Mar. 19, 2004, provisional application No. 60/602,893, filed on Aug. 19, 2004.

(51) Int. Cl.
*A61C 15/00* (2006.01)
(52) U.S. Cl. ....................................... 132/323
(58) Field of Classification Search .................. 132/323, 132/321, 324–329; 433/141
See application file for complete search history.

(56) References Cited

U.S. PATENT DOCUMENTS

| | | | |
|---|---|---|---|
| 3,533,420 A * | 10/1970 | Maloney et al. ............... | 132/325 |
| 3,949,769 A | 4/1976 | Minka | |
| 4,004,597 A | 1/1977 | Kupperman et al. | |
| 4,004,599 A | 1/1977 | Rosenfeld | |
| 4,005,721 A * | 2/1977 | Yasumoto ...................... | 132/325 |
| 4,026,308 A | 5/1977 | Krivit | |
| 4,052,994 A | 10/1977 | Thun | |
| 4,253,477 A | 3/1981 | Eichman | |
| 4,254,786 A | 3/1981 | Won | |
| 4,265,257 A | 5/1981 | Salyer | |
| 4,280,518 A | 7/1981 | Gambaro | |
| 4,304,246 A | 12/1981 | Yafai | |
| 4,427,018 A | 1/1984 | Lagace | |
| 4,434,806 A | 3/1984 | Givens | |
| 4,495,956 A | 1/1985 | Fourie | |

(Continued)

OTHER PUBLICATIONS

PCT International Search Report for LUI for PCT/US05/08967, Filed Mar. 18, 2005, Dated Aug. 2, 2005.

(Continued)

*Primary Examiner* — Cris L Rodriguez
*Assistant Examiner* — Hao D Mai
(74) *Attorney, Agent, or Firm* — Law Offices of Albert Wai-Kit Chan, PLLC

(57) ABSTRACT

The invention is dental floss applicator and interdental stimulator that is flexible and also includes a guard to ensure that the dental floss has not been used or otherwise tampered with. Users can adjust the angle of the dental floss applicator and stimulator into a configuration that best suits their particular needs. When flex adjusted, the applicator is able to hold its new configuration while maintaining sufficient strength to allow the user to comfortably maneuver the apparatus to properly floss the teeth or stimulate the gums. Furthermore, the invention is disposable, rendering it convenient to use after a meal when the user is away from a private bathroom setting, such as at a home or other lodging.

19 Claims, 11 Drawing Sheets

U.S. PATENT DOCUMENTS

Figure 1A:
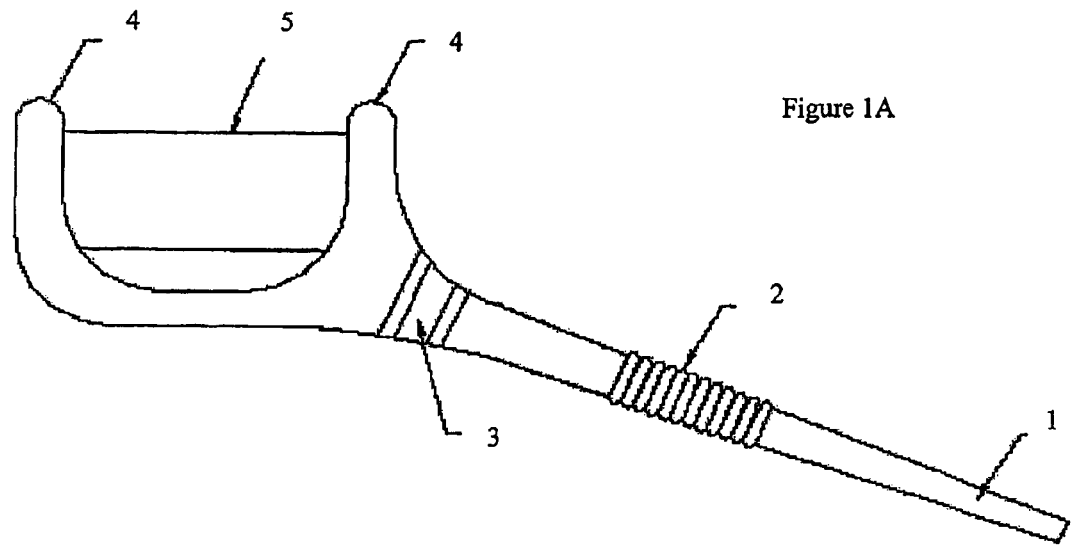

| | | |
|---|---|---|
| 4,546,782 A | 10/1985 | Kucher |
| 4,615,349 A | 10/1986 | Kukuruzinski |
| 4,657,033 A | 4/1987 | Dalton |
| 4,683,875 A * | 8/1987 | Rabinowitz .................... 601/141 |
| 4,691,719 A | 9/1987 | Ciccarelli |
| 4,706,694 A * | 11/1987 | Lambert ....................... 132/323 |
| 4,727,895 A | 3/1988 | Berarducci |
| 4,729,392 A | 3/1988 | Tenny |
| 4,736,757 A | 4/1988 | Badoux |
| 4,807,752 A | 2/1989 | Chodorow |
| 4,817,642 A | 4/1989 | Lipp |
| 4,829,621 A | 5/1989 | Phenegar |
| 4,920,992 A | 5/1990 | Preciutti |
| 4,982,752 A | 1/1991 | Rodriguez |
| 5,020,554 A | 6/1991 | Feinberg |
| 5,052,071 A | 10/1991 | Halm |
| 5,086,792 A | 2/1992 | Chodorow |
| 5,184,719 A | 2/1993 | Gordon |
| 5,261,430 A | 11/1993 | Mochel |
| 5,388,600 A | 2/1995 | Hart |
| 5,483,982 A | 1/1996 | Bennett et al. |
| 5,503,169 A | 4/1996 | Won |
| 5,538,023 A | 7/1996 | Oczkowski et al. |
| 5,579,786 A | 12/1996 | Wolk et al. |
| 5,738,124 A | 4/1998 | Cervato |
| 5,799,674 A | 9/1998 | Ali et al. |
| 5,819,769 A | 10/1998 | Gutierrez |
| 5,829,458 A | 11/1998 | Chodorow |
| 5,860,435 A | 1/1999 | Hippensteel |
| 5,881,745 A | 3/1999 | Landis |
| 5,904,153 A | 5/1999 | Meibauer |
| 5,911,229 A | 6/1999 | Chodorow |
| 5,913,418 A | 6/1999 | Singh |
| 5,931,171 A | 8/1999 | Landis et al. |
| 5,934,046 A | 8/1999 | Whittaker |
| 5,934,297 A | 8/1999 | Hippensteel |
| 5,975,296 A | 11/1999 | Dolan et al. |
| 6,006,762 A | 12/1999 | Hsia |
| D424,748 S | 5/2000 | Dolan et al. |
| 6,062,236 A | 5/2000 | Gaudet |
| 6,065,479 A | 5/2000 | Chodorow |
| 6,085,760 A | 7/2000 | Chodorow |
| 6,092,536 A | 7/2000 | Owens |
| 6,102,051 A | 8/2000 | Neves |
| 6,123,087 A | 9/2000 | Jang |
| 6,131,586 A | 10/2000 | Flanagan |
| 6,161,555 A | 12/2000 | Chen |
| 6,161,556 A | 12/2000 | Gutierrez |
| 6,220,256 B1 | 4/2001 | Dolan et al. |
| 6,234,182 B1 | 5/2001 | Berglund |
| 6,474,347 B1 | 11/2002 | Hallinder et al. |
| 6,488,036 B1 | 12/2002 | Francis |
| 6,526,994 B1 | 3/2003 | Santoro |
| 6,539,951 B2 | 4/2003 | Baillie et al. |
| 6,544,457 B1 | 4/2003 | Rieser |
| 6,571,804 B2 | 6/2003 | Adler |
| 6,572,063 B1 | 6/2003 | Gitelman |
| 6,715,603 B1 | 4/2004 | Uribe |
| 6,721,987 B2 | 4/2004 | McDevitt et al. |
| 6,729,789 B2 | 5/2004 | Gordon |
| 6,731,213 B1 | 5/2004 | Smith |
| 2004/0134512 A1 * | 7/2004 | Ding et al. .................... 132/323 |
| 2005/0217692 A1 * | 10/2005 | Chodorow et al. ........... 132/323 |

OTHER PUBLICATIONS

PCT Written OPinion of the International Searching Authority.
U.S. Publication No. US 2004/0134512 A1, Jul. 15, 2004, Ding et al., "Dental Flosser".

* cited by examiner

FLEXIBLE DENTAL FLOSS APPLICATOR AND INTERDENTAL GUM STIMULATOR

This application claims benefit of U.S. Ser. No. 60/554,636, filed Mar. 19, 2004, and U.S. Ser. No. 60/602,893, filed Aug. 19, 2004, the entire contents of which are incorporated by reference into this application.

Throughout this application, various publications are referenced and the full citations for these publications may be found in the text where they are referenced. The disclosures of these publications in their entireties are hereby incorporated by reference into this application to more fully describe the state of the art to which this invention pertains.

BACKGROUND OF THE INVENTION

Flossing and the typical manipulation of the dental floss with the hands and fingers can be uncomfortable activities that result in manual as well as oral discomfort. Because the hands and fingers are intimately involved and the activity is an invasive one involving the mouth, flossing can be a messy activity that people may feel uncomfortable in undertaking outside of a private bathroom setting, such as at home.

As a result, a variety of dental floss applicators have been developed over the years to overcome the need for insertion of the fingers in the mouth when flossing. However, it can be difficult to mimic the dexterity of the human hand with a stiff, probe-like flossing apparatus. Consequently, it may be quite difficult to properly floss the teeth situated further back in the mouth without discomfort and/or injury resulting from the pointed end to the floss applicator. There have been a number of attempts to deal with the abovementioned issues as shown in the following U.S. Patents:

U.S. Pat. No. 6,915,81 may be the first patent on a dental floss applicator design that provides a C-shaped device for a user to install dental floss. This C-shaped device is adjustable such that the dental floss can be parallel or perpendicular to the handle. The disadvantage with U.S. Pat. No. 6,915,81 is that it lacks a flexible elbow for maneuverability and a tapered end for interdental cleaning and gum stimulation.

U.S. Pat. No. 8,933,45 is an adjustable C-shaped device for a user to install dental floss. This device is designed to be attached to a toothbrush. The disadvantage with U.S. Pat. No. 8,933,45 is that it lacks a handle, a flexible elbow for maneuverability, and a tapered end for interdental cleaning and gum stimulation.

U.S. Pat. No. 1,306,998 is similar to U.S. Pat. No. 6,915,81. The disclosed C-shaped device is adjustable such that the dental floss can be parallel or perpendicular to the handle. Additionally, this design includes a built-in storage for dental floss. The disadvantage with U.S. Pat. No. 1,306,998 is that it lacks a flexible elbow for maneuverability and a tapered end for interdental cleaning and gum stimulation.

U.S. Pat. No. 1,512,633 describes a fixed dental floss applicator with one C-shaped device on each end of the applicator. One C-shaped device is parallel to the handle, while the other C-shaped device is perpendicular to it. The disadvantage with U.S. Pat. No. 1,512,633 is that it lacks a flexible elbow for maneuverability and a tapered end for interdental cleaning and gum stimulation.

U.S. Pat. No. 2,172,591 describes a dental floss applicator that is similar to the one described in U.S. Pat. No. 8,933,45. It is an adjustable C-shaped device that allows a user to install a dental floss. This device is designed to attach to a toothbrush and also includes built-in storage for dental floss. The disadvantage with U.S. Pat. No. 2,172,591 is that it lacks a flexible elbow for maneuverability and a tapered end for interdental cleaning and gum stimulation.

U.S. Pat. No. 3,368,553 describes a design similar to the one described in U.S. Pat. No. 6,915,81. It is designed to be an adjustable toothpick applicator. The disadvantage with U.S. Pat. No. 3,368,553 is that it lacks floss, a floss-applicator, a flexible elbow for maneuverability, and a tapered end for interdental cleaning and gum stimulation.

U.S. Pat. No. 4,002,183 describes a design similar to that of U.S. Pat. No. 1,512,633. It is a fixed dental floss applicator with one C-shaped device on each end of the applicator. One C-shaped device is parallel to the handle, while the other C-shaped device is perpendicular to it. It is designed to be easily-manufactured and inexpensive. The disadvantage with U.S. Pat. No. 4,002,183 is that it lacks a flexible elbow for maneuverability and a tapered end for interdental cleaning and gum stimulation.

U.S. Pat. No. 4,005,721 describes a dental floss applicator where a user installs dental floss onto the device. This device is adjustable such that the dental floss can be parallel or perpendicular to the handle. This device is interchangeable and can be replaced with a device with a different shape. The disadvantage with U.S. Pat. No. 4,005,721 is that it lacks a flexible elbow for maneuverability and a tapered end for interdental cleaning and gum stimulation.

U.S. Pat. No. 4,051,857 describes a dental floss applicator where a user installs dental floss onto the device. This device is adjustable such that the dental floss can be parallel or perpendicular to the handle. This applicator provides an improved control mechanism to control the angle of the dental floss. The disadvantage with U.S. Pat. No. 4,051,857 is that it lacks a flexible elbow for maneuverability and a tapered end for interdental cleaning and gum stimulation.

U.S. Pat. No. 4,671,307 describes an adjustable dental floss applicator with one C-shaped device on each end of the applicator. One C-shaped device is parallel to the handle, while the other C-shaped device is perpendicular to it. It is a permanent applicator that requires users to install dental floss before each use. The disadvantage with U.S. Pat. No. 4,671,307 is that it lacks a flexible elbow for maneuverability and a tapered end for interdental cleaning and gum stimulation.

U.S. Pat. No. 4,706,694 is similar to U.S. Pat. No. 6,915,81. A C-shaped device is adjustable such that the dental floss can be parallel or perpendicular to the handle and is also designed to maintain sufficient tension in the dental floss. The disadvantage with U.S. Pat. No. 4,706,694 is that it lacks a flexible elbow for maneuverability and a tapered end for interdental cleaning and gum stimulation.

U.S. Pat. No. 5,125,424 is similar to U.S. Pat. No. 6,915,81. A C-shaped device is adjustable such that the dental floss can be parallel or perpendicular to the handle. This design also allows users to install a length of dental floss as well as other devices, such as an interdental brush. The disadvantage with U.S. Pat. No. 5,125,424 is that it lacks a flexible elbow for maneuverability and a tapered end for interdental cleaning and gum stimulation.

U.S. Pat. No. 5,279,315 is similar to U.S. Pat. No. 6,915,81. A C-shaped device is adjustable such that the dental floss can be parallel or perpendicular to the handle. The design allows users to change the angle of the dental floss with more ease than the other prior art. Nevertheless, the disadvantage with U.S. Pat. No. 5,279,315 is that it lacks a flexible elbow for greater maneuverability and a tapered end for interdental cleaning and gum stimulation.

Another general disadvantage of the above-discussed designs is that the devices are permanent in nature. The permanent nature of these applicators discourages their widespread adoption since dental floss is typically disposed of after use in removing food and bacteria from the mouth. Accordingly, repeated use of a permanent dental floss applicator is not acceptable many consumers. Furthermore, the permanent nature of the applicators, factors such as size, weight, and upkeep, do not translate into convenient use for users during excursions away from the private bathroom setting.

References Cited:

United States Patents

| | | |
|---|---|---|
| 691,581 | Baumeister, Auguste | Jan. 21, 1902 |
| 893,345 | Monson, Otto J. | Jul. 14, 1918 |
| 1,306,998 | Dimitroff, Vladimir T. | Jun. 17, 1919 |
| 1,512,633 | Peckham, John A. | Nov. 15, 1924 |
| 2,172,591 | Peterson, Arthur L. | Jun. 20, 1939 |
| 3,368,553 | Kirby, James B. | Jan. 29, 1965 |
| 4,002,183 | Restall, Raymond B. | Sep. 8, 1977 |
| 4,005,721 | Yasumoto, Michio | Feb. 1, 1977 |
| 4,051,857 | Zambito, James B. | Oct. 4, 1977 |
| 4,671,307 | Curbow et al. | Jul. 15, 1985 |
| 4,706,694 | Lambert, Joseph | Mar. 24, 1986 |
| 5,125,424 | Eisen, Ewald | Mar. 26, 1991 |
| 5,279,315 | Huang, Ming-Liang | Jan. 25, 1993 |

SUMMARY OF THE INVENTION

It is an object of this invention to provide an apparatus for interdental hygiene that manipulates and applies one or more lengths of dental floss for cleaning the interstices of the teeth. In particular, it is an object of this invention to provide a dental floss applicator that is strong, but pliable, with a flexible elbow that enables sufficient maneuverability to properly floss the teeth, including the teeth in the rear of the mouth.

It is another object of this invention to provide an apparatus with a pliable tapered end, preferably pick-like, for cleaning the teeth and massaging and stimulating the gums.

It is still another object of this invention to provide an economical and disposable dental floss applicator that is convenient to carry during excursions where a user will not have ready access to a private bathroom setting. Such applicators are also suitable for dispensing by restaurants to their patrons, in the same manner as mints are freely dispensed.

It is yet another object of this invention to provide a guard on the dental floss applicator to help users identify whether a particular applicator has been used. This is important where the applicators are freely dispensed in a public setting, such as in a restaurant.

These and other objects and advantages of this invention will become apparent to those skilled in the art after considering the following detailed specification together with the accompanying drawings.

DETAILED DESCRIPTION OF THE FIGURES

FIG. 1A: Detailed design of Flexible Dental Floss Applicator and Interdental Gum Stimulator. Presented is a side view of the apparatus illustrating the detailing of the applicator and its utilitarian sections: the tapered end 1; the middle handle 2 for grip; the flexible elbow 3; and the "c" shaped applicator arms 4 through which a segment of floss 5 is to be threaded and secured.

Figure 1B:
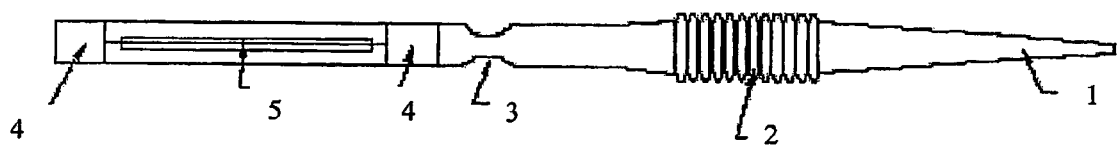

FIG. 1B: Presented is a bottom view of the apparatus illustrating the detailing of the applicator and its utilitarian sections: the tapered end; the middle handle with ridges for grip; the flexible elbow; and the "c" shaped applicator arms through which a segment of floss is to be threaded and secured.

Figure 1C:
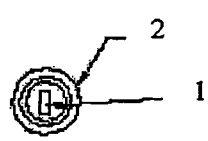

FIG. 1C: Presented is a rear view of the apparatus looking at the tapered end 1 illustrating the detailing of the applicator and its utilitarian sections: tapered end 1; the middle handle for grip 2. The tapered end 1 shown is chisel-like, but it may also be pointed.

Figure 1D:
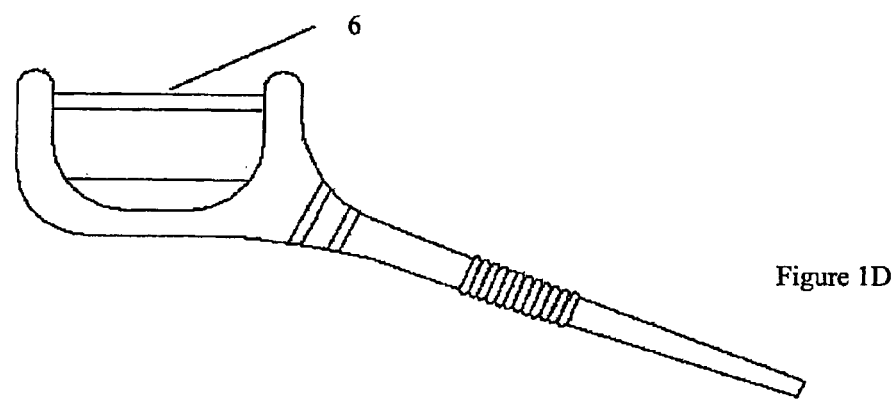

FIG. 1D: Presented is a side view of the apparatus embodying a second length of floss 6.

Figure 2A:
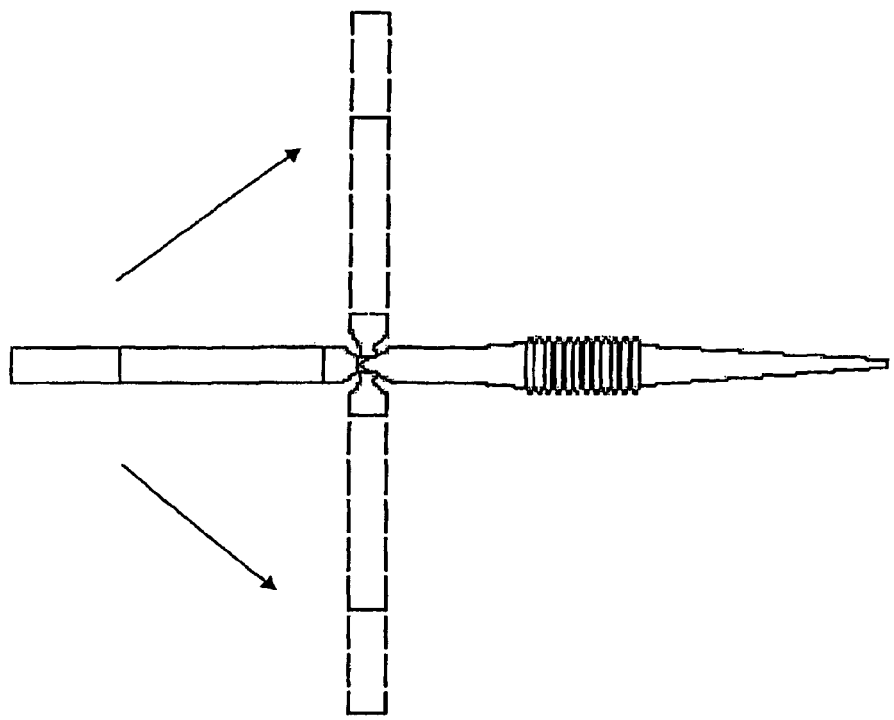

FIG. 2A: Presented is a top view of the apparatus illustrating the 0 to about 90 degree flexible sweep of the floss applicator arms in either direction permitted by the flexible elbow.

Figure 2B:
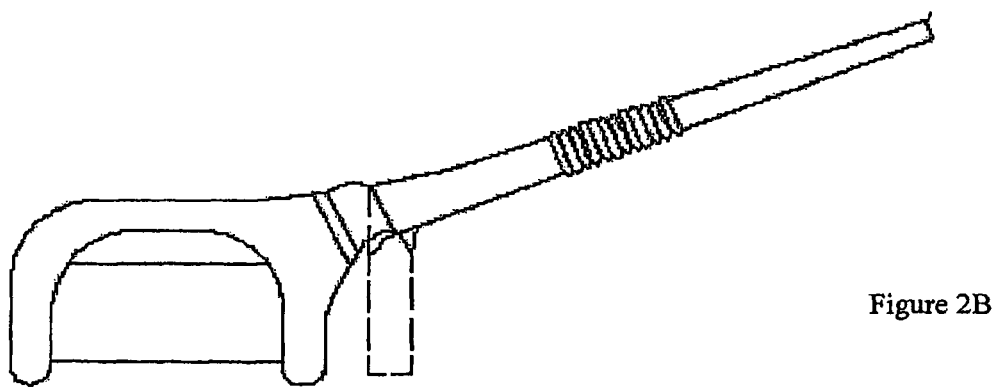

FIG. 2B: Presented is a side view of the apparatus illustrating the flexible sweep of the floss applicator arms away from the page permitted by flexible elbow.

Figure 2C:
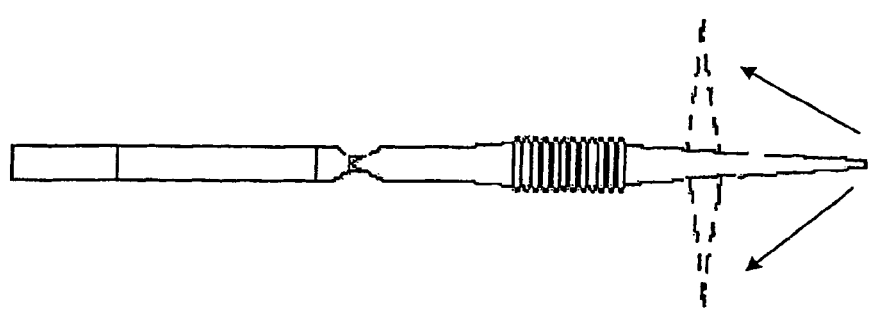

FIG. 2C: Presented is a top view of the apparatus illustrating the 0 to 90 degree flexible sweep of the tapered end in either direction.

Figure 3:
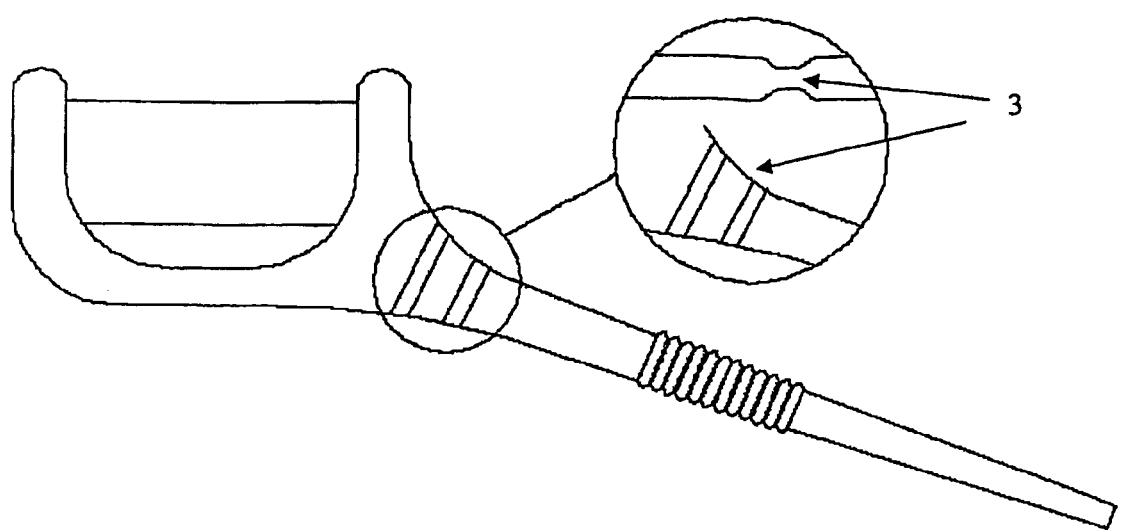

FIG. 3: Presented is a side and top view of the flexible elbow. The flexible elbow 3 may be constructed of polypropylene.

Figure 4A:
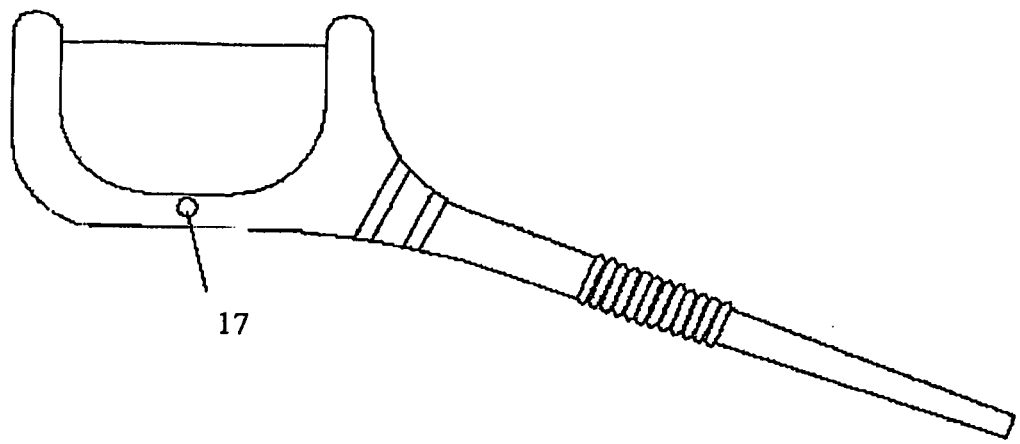

FIG. 4A: Presented is a side view of the dental floss applicator that is designed to accept a dental floss guard. There is a hole 17 on the "C" shape applicator arms to receive a locking device 20.

Figure 4B:
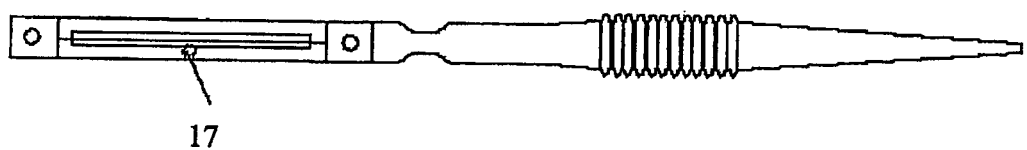

FIG. 4B: Presented is a bottom view of the dental floss applicator that is designed to accept a dental floss guard. There is a hole 17 on the "C" shape applicator arms.

Figure 4C:
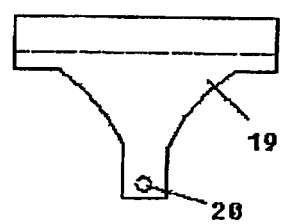

FIG. 4C: Presented is a front view of the dental floss guard 19 that is designed to protect the dental floss in the applicator in FIGS. 4A and 4B. There is a locking device 20 on the dental floss guard that secures dental floss guard onto the dental floss applicator.

Figure 4D:
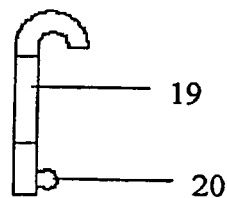

FIG. 4D: Presented is a side view of the dental floss guard 19 that is designed to protect the dental floss. There is a locking device 20 on the dental floss guard that secures dental floss guard onto the dental floss applicator.

Figure 5:
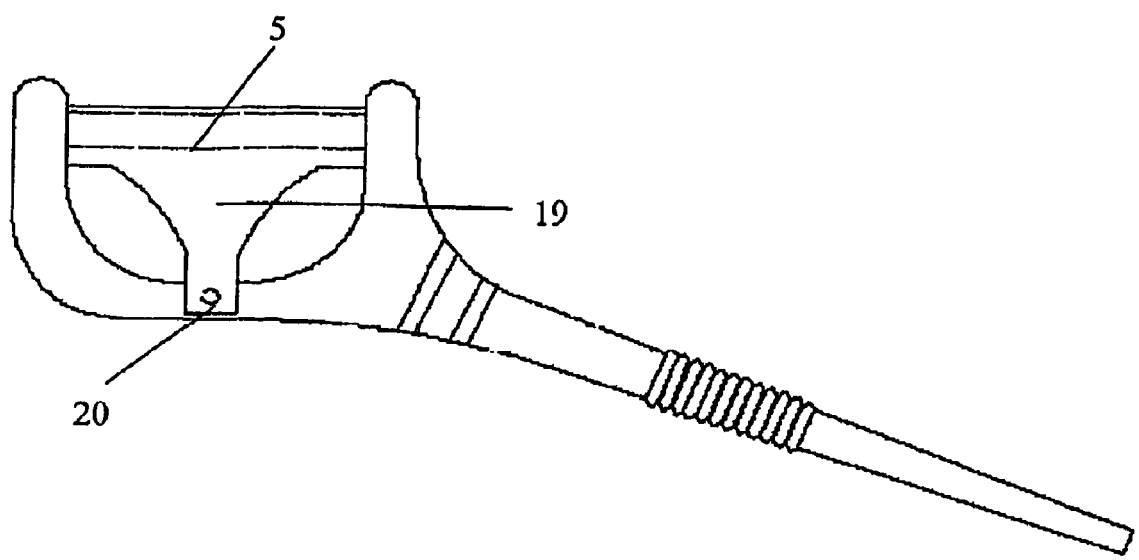

FIG. 5: Presented is a side view of the dental floss applicator with dental floss guard 19 installed. The dental floss guard 19 protects the dental floss 5 which is hidden behind the dental floss guard 5. There is a locking device 20 on the dental floss guard that secures dental floss guard onto the dental floss applicator.

Figure 6A:
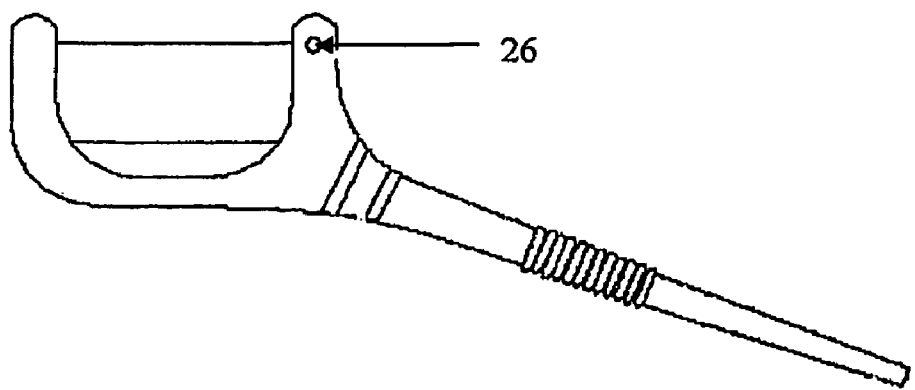

FIG. 6A: Presented is a side view of the dental floss applicator that is designed to accept a dental floss guard. There is a hole 26 on the "C" shape applicator arms to accept a locking device 28.

Figure 6B:
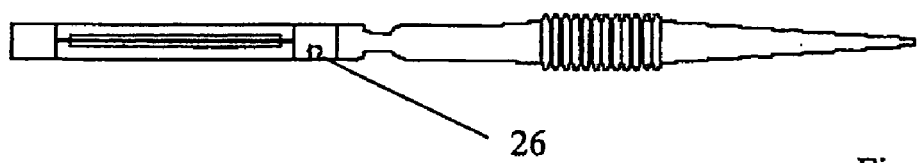

FIG. 6B: Presented is a bottom view of the dental floss applicator that is designed to accept a dental floss guard. There is a hole 26 on the "C" shape applicator arms to accept a locking device 28.

Figure 6C:
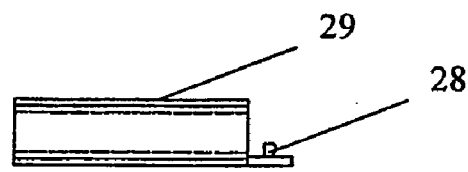

FIG. 6C: Presented is a front view of a dental floss guard 29 that is designed to protect the dental floss in the applicator in FIGS. 6A and 6B. There is a locking device 28 on the dental floss guard that secures dental floss guard onto the dental floss applicator.

Figure 6D:
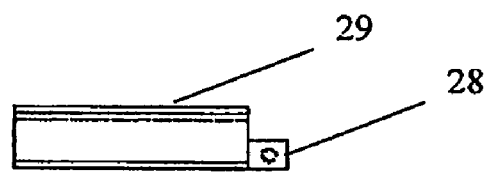

FIG. 6D: Presented is a top view of a dental floss guard 29 that is designed to protect the dental floss in the applicator in FIGS. 6A and 6B. There is a locking device 28 on the dental floss guard that secures dental floss guard 29 onto the dental floss applicator.

Figure 6E:
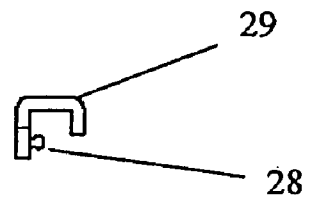

FIG. 6E: Presented is a side view of a dental floss guard that is designed to protect the dental floss in the applicator in FIGS. 6A and 6B. There is a locking device 28 on the dental floss guard that secures dental floss guard onto the dental floss applicator.

Figure 7A:
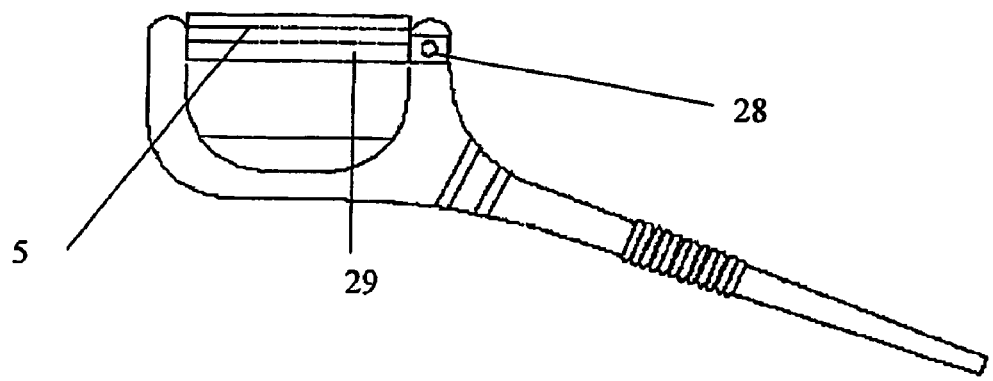

FIG. 7A: Presented is a side view of the dental floss applicator with dental floss guard 29 installed. The dental floss guard 29 protects the dental floss 5 which is hidden behind the dental floss guard 29. There is a locking device 28 on the dental floss guard that secures dental floss guard onto the dental floss applicator.

Figure 7B:
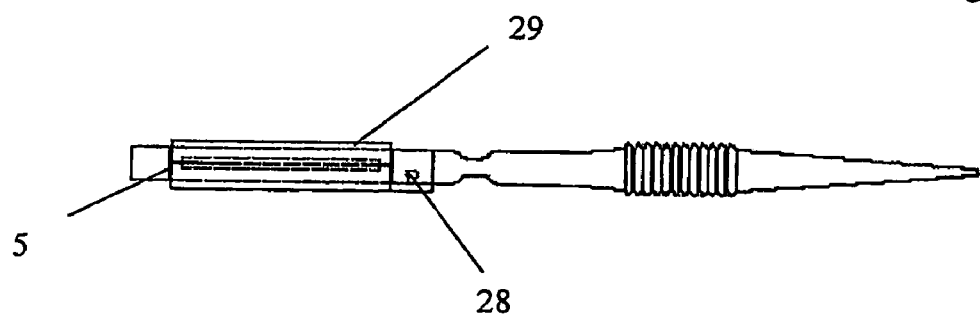

FIG. 7B: Presented is a bottom view of the dental floss applicator with dental floss guard 29 installed. The dental floss guard 29 protects the dental floss 5 which is hidden behind the dental floss guard 29. There is a locking device 28 on the dental floss guard that secures dental floss guard onto the dental floss applicator.

Figure 8A:
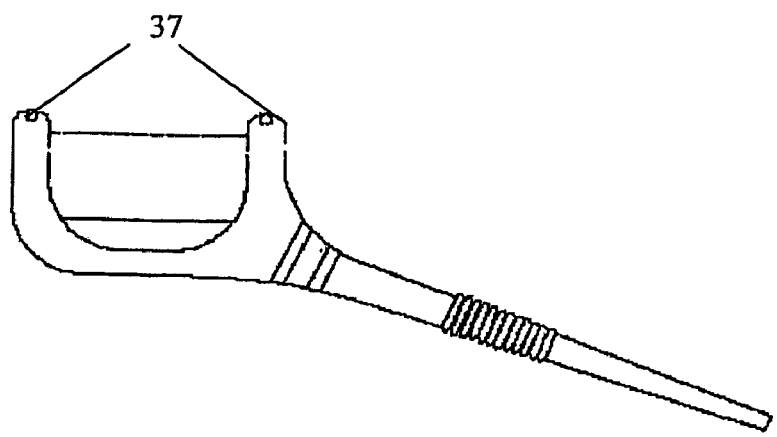

FIG. 8A: Presented is a side view of the dental floss applicator that is designed to accept the dental floss guard. There are two holes 37 on the "C" shape applicator arms to accept a locking device 39.

Figure 8B:
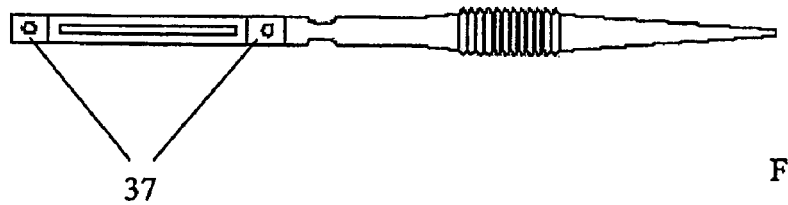

FIG. 8B: Presented is a bottom view of the dental floss applicator that is designed to accept the dental floss guard. There are two holes 37 on the "C" shape applicator arms to accept a locking device 39.

Figure 8C:
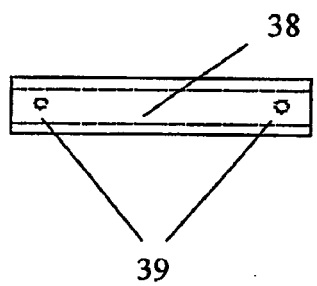

FIG. 8C: Presented is a front view of a dental floss guard 38 that is designed to protect the dental floss in the applicator in FIGS. 8A and 8B. There are two locking devices 39 on the dental floss guard that secures dental floss guard onto the dental floss applicator.

Figure 8D:
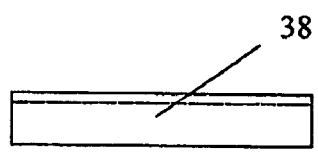

FIG. 8D: Presented is a top view of a dental floss guard 38 that is designed to protect the dental floss in the applicator in FIGS. 8A and 8B.

Figure 8E:
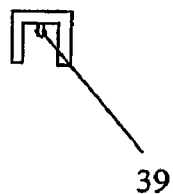

FIG. 8E: Presented is a side view of a dental floss guard that is designed to protect the dental floss in the applicator in FIGS. 8A and 8B. There are two locking devices 39 on the dental floss guard that secures dental floss guard onto the dental floss applicator.

Figure 9A:
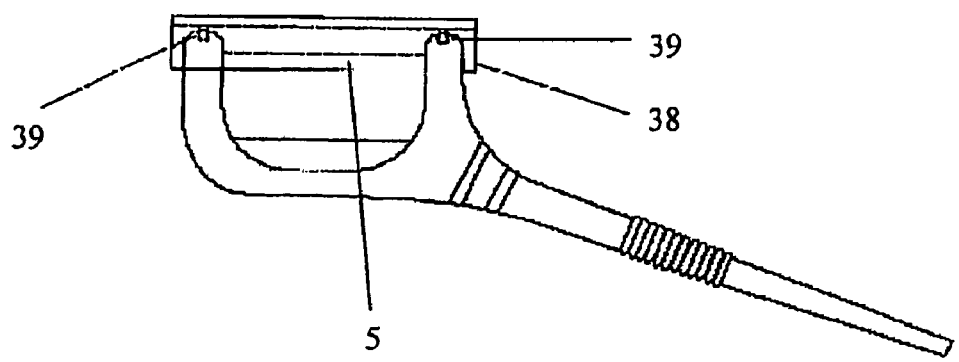

FIG. 9A: Presented is a side view of the dental floss applicator with dental floss guard 38 installed. The dental floss guard 38 protects the dental floss 5 which is hidden behind the dental floss guard 38. There are two locking devices 39 on the dental floss guard that secures dental floss guard onto the dental floss applicator.

Figure 9B:
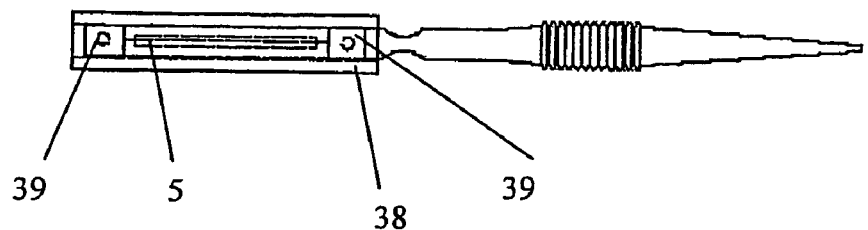

FIG. 9B: Presented is a bottom view of the dental floss applicator with dental floss guard 38 installed. The dental floss guard 38 protects the dental floss 5 which is hidden behind the dental floss guard 38. There are two locking devices 39 on the dental floss guard that secures dental floss guard onto the dental floss applicator.

Figure 10:
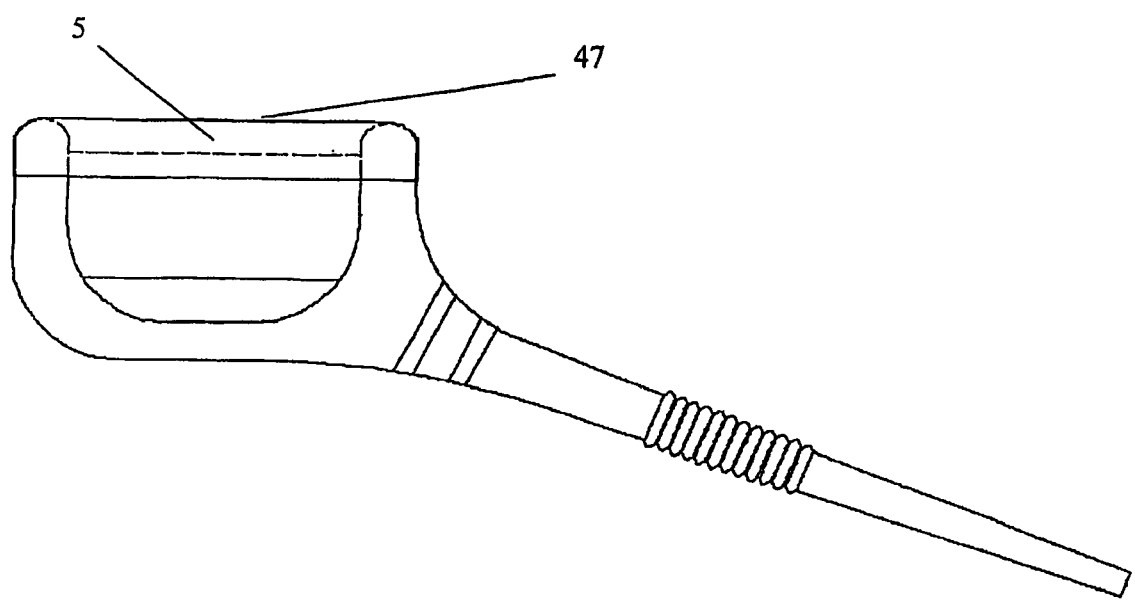

FIG. 10: Presented is a side view of a dental floss applicator with dental floss guard 47 installed. A dental floss guard 47 protects the dental floss 5 which is hidden behind a dental floss guard 47. There are no locking devices here. Instead, the dental floss guard is made of a soft material that is wrapped around and secured onto the dental floss applicator.

Figure 11A:
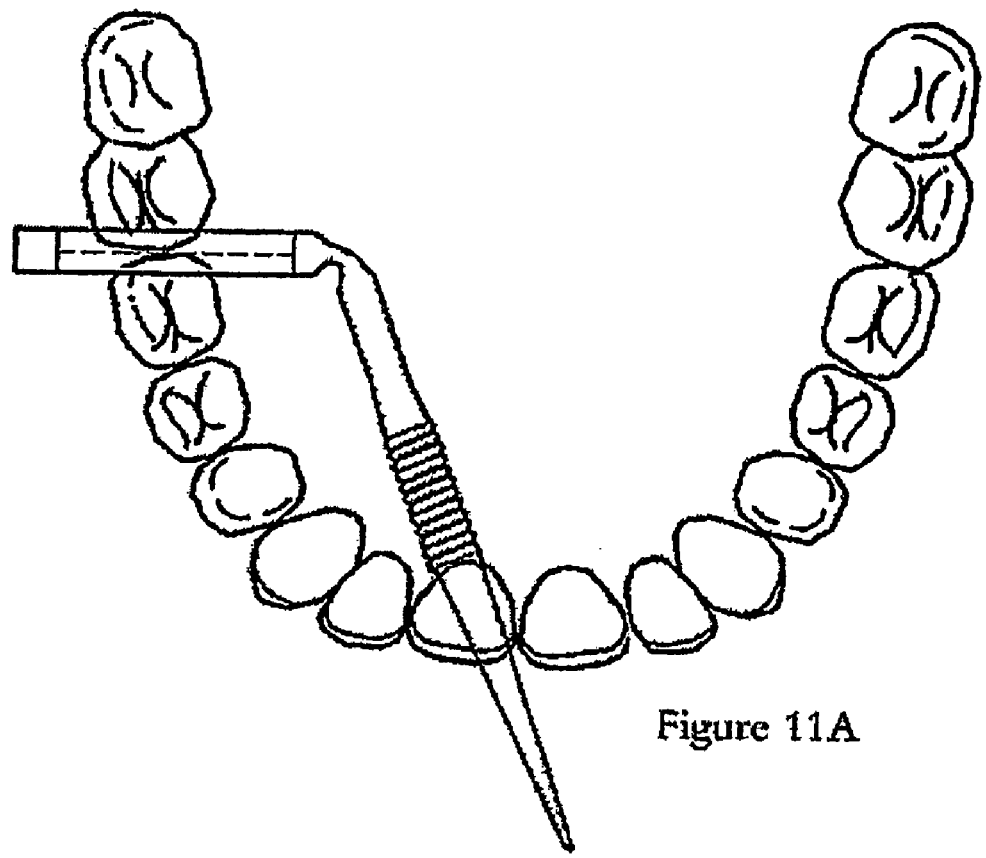

FIG. 11A: Presented is a top view of how one would floss the back teeth in the left side of the mouth with the dental floss applicator.

Figure 11B:
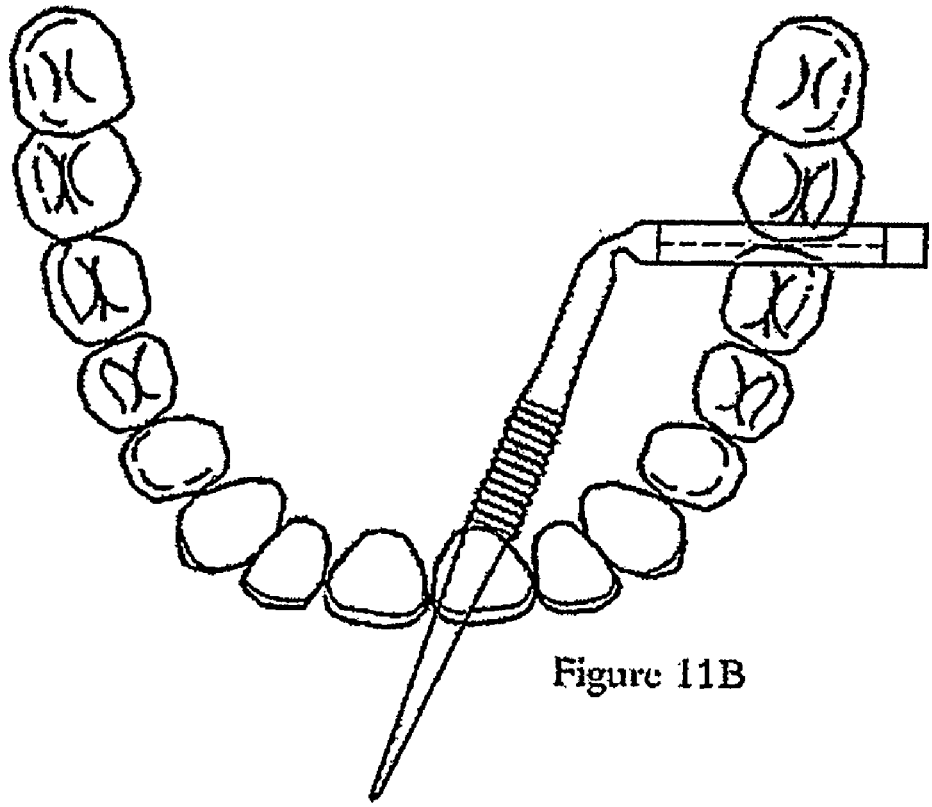

FIG. 11B: Presented is a top view of how one would floss the back teeth in the right side of the mouth with the dental floss applicator.

DETAILED DESCRIPTION OF THE INVENTION

The invention provides a dental hygiene apparatus with teeth-cleaning means and a flexible handling means whereby the teeth-cleaning means and the flexible handling means are united and pliable at their points of joinder. The teeth-cleaning means and handling means are "united" in the sense that they are brought together to form a single apparatus by joining, securing, connecting, linking, or the like. The apparatus can be of one construction or an aggregate of parts composed of the same or different material, consistent with the teachings of this disclosure.

"Pliable" means that the apparatus is flexible and receptive to change such that it is capable of being flex adjusted (bent) numerous times without breaking and will readily adhere to a new configuration after flex adjustment. The meaning will become more apparent upon reading the full disclosure and the examples contained herein.

The teeth-cleaning means comprises arms for securing one or more lengths of floss. However, the strands of material need not be limited to floss. The floss can be substituted for strands of other interdental materials, such as those related to cosmetics (e.g., whitening) or medicine for the gums. The teeth-cleaning means further comprises a tapered portion at one end of the apparatus, chisel-shaped or pointed, for use as an interdental cleaner and/or stimulator.

The invention further provides a flexible elbow and tapered end for increased maneuverability and effectiveness when cleaning the teeth. Between the flexible elbow and tapered end is the handling means which comprises a handle with ridges, grooves, or a combination thereof for the desired grip.

In one embodiment, the dental hygiene apparatus is made of one solid construction of polypropylene. It comprises a narrow, chisel-shaped feature at one end which gradually transitions and widens into a handle and before tapering to a flexible elbow adjoining the two applicator arms which secure a length of floss. The flexible elbow and chisel-shaped feature are pliable and designed to permit maximum maneuverability for the user when flossing. Many other embodiments are possible and will become apparent upon reading the entire disclosure and the examples contained herein.

Flexible Feature:

Approximately where the handle transitions into the applicator arms, there is a ridged flexible elbow that is capable of being flex adjusted into the desired position when flossing. The user need merely bend the apparatus at the flexible elbow to the desired angle. The invention is designed such that is pliable but yet remains sufficiently strong for use, despite numerous flex adjustments.

For instance, the user may flex adjust the flexible elbow anywhere from 0 to about 15 degrees when flossing the teeth in the front of the mouth. When flossing the teeth on the side, the user may desire to flex adjust the flexible elbow anywhere from about 15 to 30 or to about 45 degrees. When flossing the teeth in the rear of the mouth, the user may then desire to flex adjust the flexible elbow anywhere from about 45 to 60 or to about 90 degrees. The invention is such that the apparatus will remain at the desired angle after it is flex adjusted. When flossing the other side of the mouth, the user need merely flex adjust apparatus as described above. The apparatus can be flex adjusted multiple times and still remain strong.

The dental floss applicator is designed for single-use and thus be disposable. In most circumstances, one single dental floss applicator will last for an entire flossing session, depending on the number of flex adjustments. During a complete flossing session, users will be bending the flexible elbows to the left and the right, and to different angles. The flexible elbow is designed to withstand multiple bendings. Some users may just want to floss one or two gaps between their teeth, so they would bend the flexible elbow maybe just 2 times. Other users may bend the flexible elbow 5 times before discarding the dental floss applicator. During a typical flossing session, users may bend the flexible elbow about 10 times. During a long flossing session, users may bend it about 20 times. If the users intend to reuse the dental floss applicator, the flexible elbow should be able to last until about 40 bendings before breaking. Experiments were conducted on the prototypes of the dental floss applicators to see how many times a flexible elbow can be flex adjusted (bent) before it breaks. A group of 50 applicators were tested. The following is a summary of the results:

| Number of Times the Dental Floss Applicator were Bent | Percent of Dental Floss Applicator That Break |
| --- | --- |
| 2 | 0% |
| 5 | 0% |
| 10 | 0% |
| 20 | 0% |
| 40 | 2% |

It is important that the dental floss applicator be capable of withstanding multiple flex adjustments. Typically, a material loses much of its strength when bent multiple times. However, the present dental floss applicator is designed such that the flexible elbow remains relatively strong, stable, and rigid even after it has been bent multiple times. Experiments were conducted on the prototypes of the dental floss applicators to see how rigid the flexible elbow is after it is bent multiple times (and remains bent at 45 degrees). A group of 50 applicators were tested. The following is a summary of the results:

| Number of Times the Dental Floss Applicator were Bent | Average Force Needed to Bend Dental Floss Applicator Away from the Teeth by 30 Degrees |
| --- | --- |
| 2 | 12 lbs |
| 5 | 12 lbs |
| 10 | 12 lbs |
| 20 | 12 lbs |
| 40 | 10 lbs |

Flexible Pick:

On one end of the dental floss applicator is a tapered portion, chisel-shaped or pointed, that can be a used as a pick to clean the teeth and to stimulate the gums. The tapered portion is designed to be pliable such that a user can bend it to effectively reach the gums and interstices of the back teeth.

Typically, when people use toothpicks, the teeth in the front of the mouth do not present a challenge. However, there is difficulty in trying to reach the interstices of the back teeth because the toothpick is straight and cannot reach the rear interstices since they are essentially perpendicular to the toothpick. As a result, people will try to bend the toothpicks, but the results are limited. The toothpicks are not very flexible and can only be bent so much before they begin to splinter.

On the other hand, the flexible tapered end (pick) of the present invention (like the flexible elbow discussed previously) can be bent anywhere from 0 to about 15, 30, 45, 60, or about 90 degrees depending on which teeth and gums the user wishes to clean and stimulate.

Like the flexible elbow, the tapered end of the apparatus is designed so as to "remember" and remain in the adjusted position while it is being used. In other words, the flexible tapered end will not bounce back to its original position after one stops applying force to it.

Like the flexible elbow, the flexible tapered end is designed to withstand multiple bending. A flexible pick can be bent a number of times during a session. Some users just want to pick one or two gaps between their teeth, so they may bend the flexible pick maybe 2 times. During a longer session, users may bend it 10, 20, or more times. The flexible pick should be able to withstand 20 flex adjustments without breaking. Experiments were conducted on the prototypes of the dental floss applicators to see how many times the flexible pick can be bent before breaking. A group of 50 apparatus were tested. The following is a summary of the results:

| Number of Times the Dental Picks were Bent | Percent of Dental Picks That Break |
| --- | --- |
| 2 | 0% |
| 5 | 0% |
| 10 | 0% |
| 20 | 0% |

Preferred Material:

The flexible feature of the dental floss applicator is accomplished by using a class of polypropylene materials, possessing the desired properties of being able to "remember" a new position when flex adjusted and having the requisite strength necessary for manipulation of the applicator/stimulator while still being yielding enough to allow for the safe and gentle cleaning of the interdental spaces and proximate gum tissues. Suitable thermoplastic resins and polymers may be used to wholly or partly construct the apparatus so as to provide it with the desired characteristics described. For the present invention, polypropylene has performed particularly well. Colors can also be added to increase the appeal to users of all ages and groups. From the colors of the rainbow, pastels, or fluorescents, the applicators can be manufactured in an array of colors according to the target audience. For example, bright, "fun" colors may be used to attract a younger user by making the floss applicator appear appealing as opposed to clinical and unpleasant. For the present invention, the preferred class of polypropylene has the following physical properties:

| Physical Properties | ASTM Methods | Units | Value |
| --- | --- | --- | --- |
| Melt flow rate | D1238L | gram/10 minutes | 15 |
| Density | D792 | Gram/cm$^3$ | 0.904 |
| Tensile Strength, yield | D638 | Kg/cm$^2$ | 365 |
| Elongation, yield | D638 | % | 9 |
| Flexural modulus | D790IA | Kg/cm$^2$ | 17000 |
| Hardness, Rockwell | D785A | R scale | 100 |
| Heat deflection temperature at 4.6 kg/cm$^2$ | D648 | °C. | 100 |
| Izod impact strength, Notched | D256A | Kg-cm/cm | 2.3 |
| Mold shrinkage | D995 | % | 1.51 |

Dental Floss Guard:

A device is provided near the dental floss so as to cover it. This device is designed as a "guard" of the dental floss such that one has to remove this "guard" before one can use the dental floor applicator. This device is also designed such that it cannot be installed back onto the dental floss applicator once it is removed. The intent is to allow users to easily identify unused and/or untampered applicators. Because the applicator will be used in a semi-internal fashion (the mouth), cleanliness is a key concern.

Several designs of these guards have proved useful. In general, one or more small holes are added onto the dental floss applicator such that the dental floss guard can be installed. The dental floss guards are manufactured separately from the dental floss applicator. There are one or more locking devices designed to fit securely into the holes on the dental floss applicators. The part connecting the locking devices and the main body of the guards are designed to be thin and weak and therefore easily broken. When a user takes away the dental floss guard, the locking devices will break off but remain in the holes on the dental floss applicators. With the holes on the applicators blocked, no guard can be installed back to the dental floss applicators once it has been used or otherwise tampered with.

Another design of the dental floss guard is to make such guard with thin plastic film that will be tightly wrapped around the area around the dental floss. When a user takes away the dental floss guard, the dental floss guard would be destroyed and cannot be reused.

With this "guard," users of the dental floss applicators can be guaranteed that the dental floss applicators are new, unused, and safe.

The invention is significant because of the following reasons:

To floss in between all the teeth properly, the dental floss should be positioned ouch that it is parallel to the gap between teeth. However, the gaps between teeth in the front of mouth are perpendicular to the gaps between teeth in the back of mouth. Most existing disposable dental floss applicators have their handle parallel to the dental floss. While it is quite easy to floss in between the teeth in the front, it is all but impossible to floss the teeth in the back properly. The solution is the invention of a disposable dental floss applicator that allows the users to easily manipulate the angle of the dental floss.

This invention is significant because if the dental floss applicator is flexible, users can now adjust the applicator such that the sharp dental simulator will never point toward the vulnerable portions of the mouth, thus promoting safe use.

This invention is significant because if the dental floss applicator is flexible, it is feasible for the manufacturer to make a longer dental floss applicator. A longer dental floss applicator achieves at least two goals. 1.) It is now impossible to point the sharp dental simulator toward the mouth flesh or gums when in use because it is too long. The chance of getting hurt during flossing is reduced. 2.) Users can control the applicators without putting their fingers in their mouths. Thereby, users do not need to open their mouths extra wide during flossing, allowing them to floss more discreetly if they intend to do so in public.

Users have different preferences and needs regarding how they use dental floss. A dental floss applicator allows users to be creative in how to achieve the task of comfortably placing the dental floss between the teeth or maneuvering the interdental stimulator/pick within the mouth in a safe and comfortable manner.

The invention is pocket size, can be made disposable, and thus can be carried in public and used in a discreet and unembarrassing manner.

This invention is also significant because of the dental floss "guard" device. With this device, one can be sure that the dental floss applicators are new, unused, and safe. This further encourages users to use the dental floss applicators they are given in public establishments, such as hotels or eateries. This invention also helps users to use dental floss applicators more discreetly and to distinguish new from used applicators.

In the preferred form of the invention, the handle and applicator arm are formed from polypropylene and/or the like to define a short "c" shaped handle with applicator arms reaching off from the flexible elbow. The applicator arms do not protrude from the applicator handle like straight tines, but rather curve out in a manner visually resembling a "C" with a short handle rather than the "Y" shape employed by some existing designs.

The handle itself comprises an interdental stimulator (pick) and then widens into a thicker middle (designed for a secure grip) and then narrows down before softly angling up and transitioning into the applicator arms. At the point of transition a strong, flexible section capable of repeated bending is imbedded [or externally applied] providing for a 90 degree adjustable sweep of the applicator arms in either direction. The apparatus is such that it will respond to pressure without losing the desired angle and shape, thus allowing for easy and gentle usage. The pick is also designed to be flexible such that it can reach the back teeth and gums.

Other features and advantages of the invention will become apparent from the following description and figures which further illustrate the principles of the invention.

Production Process:

After the designs of the dental floss applicator and/or the dental floss guard are finalized, industrial grade moldings are custom made according to the final designs. Depending on the size of the moldings, a number of copies of the dental floss applicator and/or dental floss guard can be made simultaneously.

To produce the dental floss applicators, multiple lines of dental floss are placed on one side of the moldings first, then heated polymer material in liquid form is injected into the moldings to form the dental floss applicators. The dental floss applicators are then ejected from the moldings. Based on the design of the moldings, some dental floss applicators ejected from some moldings are connected by dental floss, some are not connected by dental floss. To separate the dental floss applicators connected by dental floss, one can cut the dental floss either by a sharp object or by heat.

To produce the dental floss guard, heated polymer material in liquid form is injected into the moldings to form the dental floss guards. The dental floss guards are then ejected from the moldings.

What is claimed is:

1. A dental hygiene apparatus, comprising:
  (a) an elongated handling means having a longitudinal axis;
  (b) a teeth-cleaning means comprising arms that secure one or more lengths of interdental material, wherein the interdental material is oriented longitudinally as related to the longitudinal axis of the handling means; and
  (c) a flexible means between the teeth-cleaning means and the handling means, wherein the flexible means is integral with the teeth-cleaning means and the handling means in that the flexible means, the teeth-cleaning means and the handling means are of one construction, and the flexible means is pliable so that the interdental material can be brought laterally to either side of the longitudinal axis of the handling means to have an about 90 degrees angle between the interdental material and the longitudinal axis of the handling means.

2. The apparatus of claim 1, wherein said interdental material is dental floss.

3. The apparatus of claim 1, wherein the elongated handling means comprises a tapered portion at one end.

4. The apparatus of claim 3, wherein the tapered portion is chisel-shaped or pointed.

5. The apparatus of claim 1, wherein the teeth-cleaning means is capable of adhering to a new position after flex adjustment at the flexible means.

6. The apparatus of claim 1, further comprises a guarding means for preventing a user from using the teeth-cleaning means.

7. The apparatus of claim 6, wherein the guarding means comprises a locking device that fits into one or more mating recesses on the teeth-cleaning means.

8. The apparatus of claim 6, wherein the guarding means comprises a thin material that securely covers parts of the teeth-cleaning means and cannot be removed without destruction of said material.

9. An dental hygiene apparatus, comprising:
(a) an elongated handle having a longitudinal axis;
(b) a cleaning head comprising two arms capable of securing one or more lengths of interdental material, wherein the interdental material is oriented longitudinally as related to the longitudinal axis of the handle; and
(c) a flexible elbow between the cleaning head and the elongated handle, wherein the flexible elbow is integral with the cleaning head and the elongated handle in that the flexible elbow, the cleaning head and the elongated handle are of one construction, and the flexible elbow is pliable so that the interdental material can be brought laterally to either side of the longitudinal axis of the handle to have an about 90 degrees angle between the interdental material and the longitudinal axis of the handle.

10. The apparatus of claim 9, wherein said interdental material is dental floss.

11. The apparatus of claim 9, wherein the elongated handle comprises a tapered end which is integral with the elongated handle.

12. The apparatus of claim 11, wherein the tapered end is chisel-shaped or pointed.

13. The apparatus of claim 11, wherein the tapered end is pliable so that it can be bent about 90 degrees to the right or to the left.

14. The apparatus of claim 9, wherein the elongated handle comprises ridges, grooves, or a combination thereof.

15. The apparatus of claim 9, wherein the apparatus, in whole or in part, is constructed of a thermoplastic resin.

16. The apparatus of claim 9, wherein the cleaning head is capable of adhering to a new position after flex adjustment at the flexible elbow.

17. The apparatus of claim 9, further comprises a guarding means for preventing a user from using the cleaning head.

18. The apparatus of claim 17, wherein the guarding means comprises a locking device that fits into one or more mating recesses on the cleaning head.

19. The apparatus of claim 17, wherein the guarding means comprises a thin material that securely covers parts of the cleaning head and cannot be removed without destruction of said material.

* * * * *